(12) United States Patent
Venkatraman et al.

(10) Patent No.: US 11,565,017 B2
(45) Date of Patent: Jan. 31, 2023

(54) AIR DECONTAMINATION DEVICE

(71) Applicant: BIOMONETA RESEARCH PVT LTD, Bangalore (IN)

(72) Inventors: Srividya Janani Venkatraman, Bangalore (IN); Arindam Ghatak, Kolkata (IN); Santanu Datta, Bangalore (IN); Ramesh Srinivasan, Bangalore (IN); Kadambi Sarangapani Ramanujan, Bangalore (IN); Srikrishnan Raghunathan, Bangalore (IN); Jayateerth Joshi, Bidar (IN)

(73) Assignee: BIOMONETA RESEARCH PVT LTD., Karnataka (IN)

( * ) Notice: Subject to any disclaimer, the term of this patent is extended or adjusted under 35 U.S.C. 154(b) by 872 days.

(21) Appl. No.: 16/462,184

(22) PCT Filed: May 11, 2018

(86) PCT No.: PCT/IN2018/050296
§ 371 (c)(1),
(2) Date: May 17, 2019

(87) PCT Pub. No.: WO2018/207215
PCT Pub. Date: Nov. 15, 2018

(65) Prior Publication Data
US 2019/0275190 A1    Sep. 12, 2019

(30) Foreign Application Priority Data

May 12, 2017  (IN) .............................. 201741016833

(51) Int. Cl.
*B03C 3/017* (2006.01)
*A61L 9/22* (2006.01)
(Continued)

(52) U.S. Cl.
CPC ................. *A61L 9/22* (2013.01); *A61L 2/232* (2013.01); *A61L 2/238* (2013.01)

(58) Field of Classification Search
CPC .................................................... B03C 3/017
(Continued)

(56) References Cited

U.S. PATENT DOCUMENTS 9,040,008 B2     5/2015  Zahedi
2002/0150520 A1  10/2002 Taylor et al.
(Continued)

FOREIGN PATENT DOCUMENTS

CN    204972385 U    1/2016
FI      20165186 A *  9/2017 ............... B03C 3/12
(Continued)

*Primary Examiner* — Gregory E Webb
(74) *Attorney, Agent, or Firm* — D'Ambrosio & Menon, PLLC; Usha Menon

(57) ABSTRACT

An air decontamination device (100) comprising: an input unit (102); an output unit (103); and a decontamination unit (104) coupled at a first end (122) to the input unit (102) and coupled at a second end (124) to the output unit (103). The decontamination unit (104) comprises: pairs of conducting plates (108), where one conducting plate of each pair is for being positively charged and the other conducting plate of each pair is for being negatively charged. The positively charged plate and negatively charged plate are separated to form an airflow path (212) and a 3D material (110) that is capable of being potentiated by static electric field is coupled to each side of conducting plate (108). When the static electric filed is applied, the surface moieties of the 3D material (110) are realigned to a direction of the static electric field to potentiate the antimicrobial activity of the 3D material (110) for destroying the microbes present in the received air.

15 Claims, 15 Drawing Sheets

(51) Int. Cl.
*A61L 2/232* (2006.01)
*A61L 2/238* (2006.01)

(58) Field of Classification Search
USPC .................................................. 422/186.07
See application file for complete search history.

(56) References Cited

U.S. PATENT DOCUMENTS

| | | |
|---|---|---|
| 2006/0070526 A1 | 4/2006 | Hong et al. |
| 2010/0282083 A1 | 11/2010 | Edwards |
| 2012/0000782 A1 | 1/2012 | Hong |
| 2013/0071298 A1 | 3/2013 | Tanimura et al. |

FOREIGN PATENT DOCUMENTS

| | | |
|---|---|---|
| JP | H06174252 A | 6/1994 |
| JP | 2015188883 A | 11/2015 |
| KR | 20040098397 A | 11/2004 |
| KR | 101187035 B1 | 9/2012 |
| RU | 2121115 C1 | 10/1998 |
| WO | 9903590 A1 | 1/1999 |
| WO | 2006102815 A1 | 10/2006 |
| WO | 2010093796 A1 | 8/2010 |
| WO | 2012122045 A2 | 9/2012 |
| WO | 2016138228 A1 | 9/2016 |

\* cited by examiner

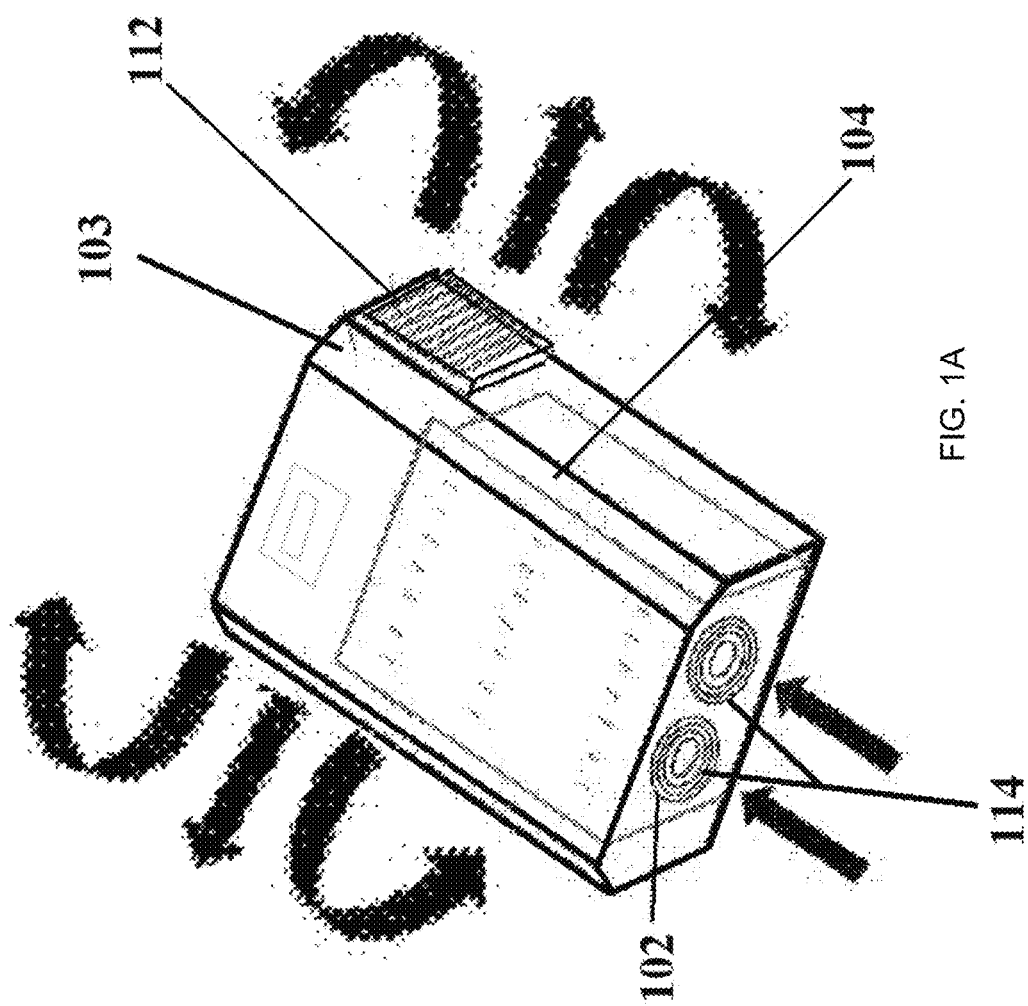

```
┌─────────────────────────────────────────────────────────┐
│ RECEIVEING, USING AN INPUT UNIT, AIR FROM ENVIRONMENT   │
│ THROUGH A PLURALITY OF AIR INLET VENTS                  │
│ 902                                                     │
└─────────────────────────────────────────────────────────┘
                            │
                            ▼
┌─────────────────────────────────────────────────────────┐
│ SEPERATING A POSITIVELY CHARGED CONDUCTING PLATE AND A  │
│ NEGATIVELY CHARGED CONDUCTING PLATE BY A DISTANCE THAT  │
│ RANGES BETWEEN 8 MM TO 12 MM TO FORM AN AIRFLOW PATH    │
│ INSIDE A DECONTAMINATION UNIT                           │
│ 904                                                     │
└─────────────────────────────────────────────────────────┘
                            │
                            ▼
┌─────────────────────────────────────────────────────────┐
│ COUPLING THE THREE DIMENSIONAL (3D) MATERIAL TO BOTH    │
│ SURFACES OF EACH OF THE POSITIVELY CHARGED CONDUCTING   │
│ PLATE AND THE NEGATIVELY CHARGED CONDUCTING PLATE       │
│ 906                                                     │
└─────────────────────────────────────────────────────────┘
                            │
                            ▼
┌─────────────────────────────────────────────────────────┐
│ APPLYING A STATIC ELECTRIC FIELD IN THE RANGE OF 2.7    │
│ KILOVOLT/CENTIMETRE (KV/CM) TO 4.2 KV/CM FOR 15 MINUTES │
│ TO 30 MINUTES, TO (I) FUNCTIONALLY EXERT A FORCE ON THE │
│ CHARGED MICROBIAL CELLS PRESENT IN THE AIR AND TRAP THE │
│ OPPOSITELY CHARGED MICROBIALS CELLS, ON THE POSITIVELY  │
│ CHARGED CONDUCTING PLATE AND THE NEGATIVELY CHARGED     │
│ CONDUCTING PLATE, DUE TO ATTRACTION BETWEEN CHARGES OF  │
│ THE MICROBIAL CELLS AND THE CHARGES OF POSITIVELY       │
│ CHARGED CONDUCTING PLATE AND THE NEGATIVELY CHARGED     │
│ CONDUCTING PLATE, AND (II) ENHANCE THE SURFACE MOIETIES │
│ DIPOLE OF THE THREE DIMENSIONAL MICROBIOCIDAL MATERIAL  │
│ TO COMPLETE REALIGNMENT TO A DIRECTION OF THE STATIC    │
│ ELECTRIC FIELD TO POTENTIATE THE MICROBIAL ACTIVITY OF  │
│ THE THREE DIMENSIONAL MATERIAL TO KILL THE MICROBIAL    │
│ CELLS THAT ARE TRAPPED OR DEPOSITED ON THE POSITIVELY   │
│ CHARGED CONDUCTING PLATEAND THE NEGATIVELY CHARGED      │
│ CONDUCTING PLATE AND TO REDUCE A LEVEL OF THE MICROBIAL │
│ CELLS INSIDE THE DECONTAMINATION UNIT BY OVER A BILLION │
│ FOLD                                                    │
│ 908                                                     │
└─────────────────────────────────────────────────────────┘
```

FIG. 9

AIR DECONTAMINATION DEVICE

BACKGROUND

Technical Field

The present invention relates to a device for reducing airborne microbes and, in particular, relates to an air decontamination device with microbiocidal functions.

Description of the Related Art

Nosocomial infection is a type of infection caused by microorganisms contracted in the environment of a healthcare facility. These infections can spread in hospital environments, nursing homes, rehabilitation facilities, clinics, or other health-care settings. The infection can originate from the outside environment, from an infected patient, or from staff who may be infected, and can spread to a susceptible person in the clinical setting. These infections can be developed by any person exposed to microorganisms like bacteria, fungi, or viruses present in the hospital. The microorganisms can spread easily through air, water or physical contact and infect a new host. Nosocomial infections may be endogenous, i.e., arising from an infectious agent present within a patient's body, or exogenous, i.e., transmitted via another source, such as staff, students, visitors, and voluntary workers, within the hospital. These infections are typically caused by microbial aerosols or microbes that deposit on a surface. Common examples of nosocomial infections include, hospital acquired pneumonia, ventilator associated pneumonia, urinary tract infection, gastroenteritis, puerperal fever, infection caused by methicillin resistant *staphylococcus aureus* (MRSA) and the like. The pathogens known to cause such nosocomial infections include *Staphylococcus aureus, Methicillin resistant Staphylococcus aureus, Candida albicans, Pseudomonas aeruginosa, Acinetobacter baumannii, Clostridium difficile, Escherichia coli, Mycobacterium tuberculosis*, Vancomycin-resistant *Enterococcus*, etc.

Pathogens that cause nosocomial infections can easily spread through the air. Since many patients admitted to the hospital are immune-compromised, it makes them more susceptible to the pathogens. Inadequate sanitary or hygiene conditions at the hospital, overcrowding, improper procedures being followed by staff, interaction with other patients, etc., contribute to development of nosocomial diseases in health-care settings.

The worldwide mortality rate due to nosocomial infections is on a rise and the infection rate in Intensive Care Units (ICUs) is particularly high. In developing countries, about 30% of all deaths in ICUs are due to nosocomial infections. Various stringent protocols are proposed for cleaning and maintenance of ICUs such as periodic floor cleaning with sterilizing solutions, surface sanitation and isolation of patients with drug resistant infections. Further, nosocomial infections can be prevented by implementing air decontamination systems to reduce microbial contamination dispersed by air. Airborne spread of nosocomial infections is not restricted to respiratory infections. Organisms causing a variety of infections can be carried by air currents to contaminate areas far from the original source.

The other kind of health hazard due to aerosolized microbes relates to the presence of large numbers of people in enclosed spaces like airplanes, theaters and malls or even office space. Additionally, with the advent of home care for the elderly or those that are immune compromised, the surrounding environment is required to be free from pathogens.

In addition to healthcare facilities, microbial control is needed in several high-end manufacturing and storage facilities. These include culture rooms, drug preparation units, and drug storage units. These units typically require a clean room environment with a continuous supply of sterile air. Warehouses that store medical supplies, food or agricultural produce require a reliable cold chain to prevent surface contamination or product degradation due to the presence of microbes. Reliable cold storage is expensive and technically challenging, especially in rural/semi-urban areas.

The air purifiers as known in art that remove microbes, hereinafter called microbial air purifiers, typically remove microbes using two techniques, namely filtration and incineration. In filtration, the air is typically sucked into the microbial air purifier and filtered using fine sieves with the capacity to filter out particles larger than 0.3 µm. These are especially useful in removing bacteria and molds from the air. The filters could then be irradiated with ultraviolet (UV) light using, for example, in-built UV lamps to inactivate the microbes on the sieves. In microbial air purifiers based on incineration, air is drawn into the purifier and subjected to heat of about 200° C. This kills the microbes in the air, hence sterilizing it. The air is then cooled to a comfortable temperature before releasing it back into circulation. Another type of air purifier used in industrial settings is the Electrostatic Precipitator (ESP). ESPs are particulate collection devices which collect particles, such as dust in air, by charging the particles and collecting them on charged plates.

Such filter-based microbial air purifiers typically also reduce speed of flow of air, that cause pressure drop, and are susceptible to clogging. Further, the microbial air purifiers as described above are typically expensive and bulky. Further, while ESPs collect and remove particulate matter from air, they typically do not inactivate or attenuate microorganisms. Microorganisms tend to accumulate over the charged plates and can form bioaerosols within the ESPs. Additionally, ESPs are bulky, inflexible to change in operating condition once installed, and associated with high capital costs. ESPs and microbial air purifiers are also associated with high power consumption. The high-power consumption is required for operation of the ventilation units, UV lamps, heating elements, coolers, particle charging units, such as corona discharge, and the like. ESPs are, typically, not used in hospitals for reasons as mentioned above. Therefore, in general, the microbial air purifiers are used in surgical settings, such as operating theatres (OTs) to provide a sterile atmosphere. However, as most hospitals and medical care centers lack infrastructure, these microbial air purifiers are not installed in other settings, such as Intensive Care Units (ICUs), outpatient wards, and the like. Therefore, patients in such settings are susceptible to hospital acquired infection, also called nosocomial infections.

Some other filters used in the purifiers are filters coated with natural *Euscaphis japonica* extract nano-particles containing quercetin-3-O-glucuronide and kaempferol-3-O-glucoside, filters made of graphene-poly(methyl methacrylate) fibres and filter made up of Polypropylene, coated with silver nitrate.

Further, most other hospital zones are equipped with regular air handling systems that do not have the capacity to reduce or eliminate environmental microbial contamination to the levels required by immune compromised patients. For example, filters mandated for routine use in ICUs, having a Minimum Efficiency Reporting Value (MERV) of 13-14, clear *S. aureus* bacteria with an efficiency of 84.9%, and clear *P. aeruginosa* and *Klebsiella* with efficiencies of only 60% and 74.2%.

The decontamination provided by these air filters as known in art is insufficient in preventing incidence of nosocomial infections. Hence, there is an urgent unmet need to further reduce the microbial contamination in health-care settings, to improve recovery rates and reducing hospital stay of the patients. In particular, air decontamination devices which have high efficiencies and reduce bacterial, fungal and viral contamination by killing the microbes are required.

SUMMARY

In accordance with the present subject matter, to overcome the problems as mentioned above, the present subject matter provides an air decontamination device.

In one embodiment, the present invention provides an air decontamination device. The air decontamination device includes an input unit, an output unit, a decontamination cassette and a 3D material. The input unit receives air from environment through a plurality of air inlets. An air flow path is established through the air decontamination device and at the end of this flow path the air passes through the output unit. The decontamination cassette comprises a first end that is adapted to couple with the input unit and a second end adapted to couple with the output unit. The decontamination cassette comprises a plurality of conducting plates in the air flow path. A static DC or a time varying AC voltage in the range of 2.7 kV to 4.2 kV from a high voltage AC/DC power source is applied between the conducting plates to ensure that one plate is positively charged and the other is negatively charged, thus setting up an electric field that ranges from 2.7 KiloVolt/centimetre (kV/cm) to 4.2 kV/cm between each pair of the conducting plates. The magnitude of the electric field is dependent on a gap maintained between the conducting plates and the gap between the conducting plates is in the range of 08 millimeter (mm) to 12 mm, in an embodiment. The airflow path inside the decontamination unit is confined to the same plane as the plurality of pairs of conducting plates, and the electric field is perpendicular to the air flow path. In an embodiment, the plane of the positively charged conducting plate is aligned parallel to the plane of the negatively charged conducting plate. The three dimensional (3D) material is coupled to both surfaces of each of the positively charged conducting plate and the negatively charged conducting plate. The three dimensional material is coated on the surface and its three dimensional structure with chemical moieties for imparting microbiocidal activity to both surfaces of the positively charged conducting plate and the negatively charged conducting plate.

The static electric field in the range of 2.7 kV/cm to 4.2 kV/cm is applied for 15 minutes to 30 minutes, to functionally exert a force on the charged microbial cells present in the air and to trap the oppositely charged microbials cells, on the positively charged conducting plate and the negatively charged conducting plate, due to attraction between charges of the microbial cells and the charges of positively charged conducting plate and the negatively charged conducting plate, and to enhance the surface moieties dipole of the three dimensional material to complete realignment to a direction of the static electric field to potentiate the antimicrobial activity of the three dimensional material for killing the microbial cells that are trapped or deposited on the positively charged conducting plate and the negatively charged conducting plate and for reducing a level of the microbial cells inside the decontamination unit by over a billion fold.

In other words, the mildly inherent microbiocidal activity due to the chemical moieties embedded in the three dimensional material is greatly enhanced by the electric field. The enhancement is enabled by the electric field that is set up by the static voltage and the gap between the positively and negatively charged conducting plates, and this electric field exerts a force on the microbial cells present in the air which is flowing through this electric field between the 3D material coupled to the parallel conducting plates. This force is created because the surface of live microbial cells has a non-zero electric potential called the zeta potential and is known in the art. This force on the microbial cells passing through the air flow path is perpendicular to the flow of the air to be decontaminated thus trapping the microbial cells on the three dimensional surface with chemical moieties and the cells are killed. The mechanism in the air decontamination device killing the microbes is attributed to the surface moieties of the three dimensional material that is realigned to a direction of the static electric field due to directional alignment of an electric dipole, to potentiate the antimicrobial activity of the three dimensional material for killing the microbial cells and for reducing a level of the microbial cells inside the decontamination unit by over a billion fold within 15 minutes to 30 minutes.

In an embodiment, a sieve may be provided between the input unit and the decontamination unit. In another embodiment, the sieve allows particles having a size less than $10^{-2}$ centimetre (cm) inside the decontamination unit.

In yet another embodiment, the input unit and the output unit may comprise a ventilation unit. In yet another embodiment, the decontamination unit comprises insulated support plates to support and hold the plurality of pairs of conducting plates in position.

In yet another embodiment, the output unit comprises a plurality of sensors for sensing temperature, humidity, microbial content in the decontaminated air. The air decontamination device comprises a microcontroller to increase or decrease a rate of delivery of the decontaminated air based on the sensed data of temperature, humidity and microbial load.

In an embodiment, the electrical power source is selected from one of a DC power source, AC power source, and pulsed power source.

In another embodiment, the AC power source has a frequency in a range of 50 Hertz (Hz) to 1000 Hz.

In yet another embodiment, the pulsed power source has 5-50% duty cycle, frequency of 1 kilo Hertz (kHz)-30 kHz and amplitude of 1 kV-5 kV.

In yet another embodiment, the DC power source and AC power source is of 1000 V-5000 V.

In yet another embodiment, when a distance between the positively charged conducting plate and the negatively charged conducting plate is 8 mm, the static electric field of 2.7 kV/cm is generated upon supplying a voltage of 2.16 kV to the plurality of the conducting plates, or when a distance between the positively charged conducting plate and the negatively charged conducting plate is 8 mm, the static electric field of 4.2 kV/cm is generated upon supplying a voltage of 3.36 kV to the plurality of conducting plates.

In yet another embodiment, when a distance between the positively charged conducting plate and the negatively charged conducting plate is 12 mm, the static electric field of 2.7 kV/cm is generated upon supplying a voltage of 3.24 kV to the plurality of conducting plates, or when a distance between the positively charged conducting plate and the negatively charged conducting plate is 12 mm, the static electric field of 4.2 kV/cm is generated upon supplying a voltage of 5.04 kV to the plurality of conducting plates. Similarly, the electric field in the range of 2.7 kV/cm to 4.2 kV/cm is generated upon supply of appropriate voltage with respect to the inter-plate distance between the conducting plates.

In an embodiment, the three dimensional material is a microbiocidal composition coated on each of the plurality of pairs of conducting plates.

In yet another embodiment, the three dimensional material is a fabric comprising a microbiocidal agent coated thereon.

In yet another embodiment, the three dimensional material is a composite material comprising multiple layers, for augmentation of surface moieties to cross-link with a microbiocidal agent.

In an embodiment, the microbiocidal agent is selected from the group comprising: bactericides, fungicides, quaternary ammonium salts, such as 3-(trimethoxysilyl) propyl-N-octadecyl-N, N-5 dimethyl ammonium chloride, 3-(trimethoxysilyl) propyl-N-tetradecyl-N,N-dimethyl ammonium chloride, 3-(trimethoxysilyl) propyl-N,N-didecyl-N-methyl ammonium chloride, 3-(trihydroxysilyl) propyl-N-octadecyl-N,N-dimethyl ammonium chloride, or a combination thereof.

In one aspect, the present disclosure provides a method of applying static electric field to air decontamination device to kill microbial cells and to reduce a level of microbial cell by over a billion fold, wherein the air decontamination device comprises an input unit for receiving air from environment through a plurality of air inlet vents;

an output unit for providing decontaminated air;

a decontamination cassette that comprises a first end that is adapted to couple with the input unit, a second end that is adapted to couple with the output unit;

a plurality of pairs of conducting plates, wherein each pair of conducting plates comprises a positively charged conducting plate, and a negatively charged conducting plate, wherein the positively charged conducting plate, and the negatively charged conducting plate are charged when a static electric field that ranges from 2.7 KiloVolt/centimetre (kV/cm) to 4.2 kV/cm is applied, wherein the plane of the positively charged conducting plate is aligned parallel to the plane of the negatively charged conducting plate, wherein the positively charged conducting plate and the negatively charged conducting plate are separated by a distance that ranges between 8 mm to 12 mm to form an airflow path inside the decontamination unit; and a three dimensional (3D) material that is coupled to both surfaces of each of the positively charged conducting plate and the negatively charged conducting plate, wherein the three dimensional material comprises surface moieties for imparting microbiocidal activity to both surfaces of the positively charged conducting plate and the negatively charged plate the method comprising:

applying the static electric field in the range of 2.7 KiloVolt/centimetre (KV/cm) to 4.2 KV/cm for 15 minutes to 30 minutes, to functionally exert a force on the charged microbial cells present in the air and trap the oppositely charged microbials cells, on the positively charged conducting plate and the negatively charged conducting plate, due to attraction between charges of the microbial cells and the charges of the positively charged conducting plate and the negatively charged conducting plate, and enhance the surface moieties dipole of the three dimensional microbiocidal material to complete realignment to a direction of the static electric field to potentiate the microbial activity of the three dimensional material to kill the microbial cells that are trapped or deposited on the positively charged conducting plate and the negatively charged conducting plate and to reduce a level of the microbial cells inside the decontamination unit by over a billion fold.

The static electric field in the range of 2.7 KiloVolt/centimetre (KV/cm) to 4.2 KV/cm reduces a level of microbes inside the decontamination unit when it is applied for 15 minutes to 30 minutes. The static electric field has advantages over the pulsed electric field which inactivates the bacterial cell by the formation of multiple pores on the cellular surface and does not alter the macromolecular structures, results in ineffective killing of microbes. Whereas, the present disclosure generates effective static electric field by function of applied voltage and distance between the positively charged conducting plate and negatively charged conducting plate and effectively reduces the microbial level inside the decontaminant unit by over a billion fold within 30 minutes.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 1a to 1d illustrate the construction of an air decontamination device of the present subject matter, in accordance with an implementation of the present subject matter;

FIG. 9 illustrates a method of applying static electric field to an air decontamination device to kill microbial cells and to reduce a level of microbial cell by over a billion fold in accordance with an implementation of the present subject matter.

DETAILED DESCRIPTION OF PREFERRED EMBODIMENTS

Figure 1B:
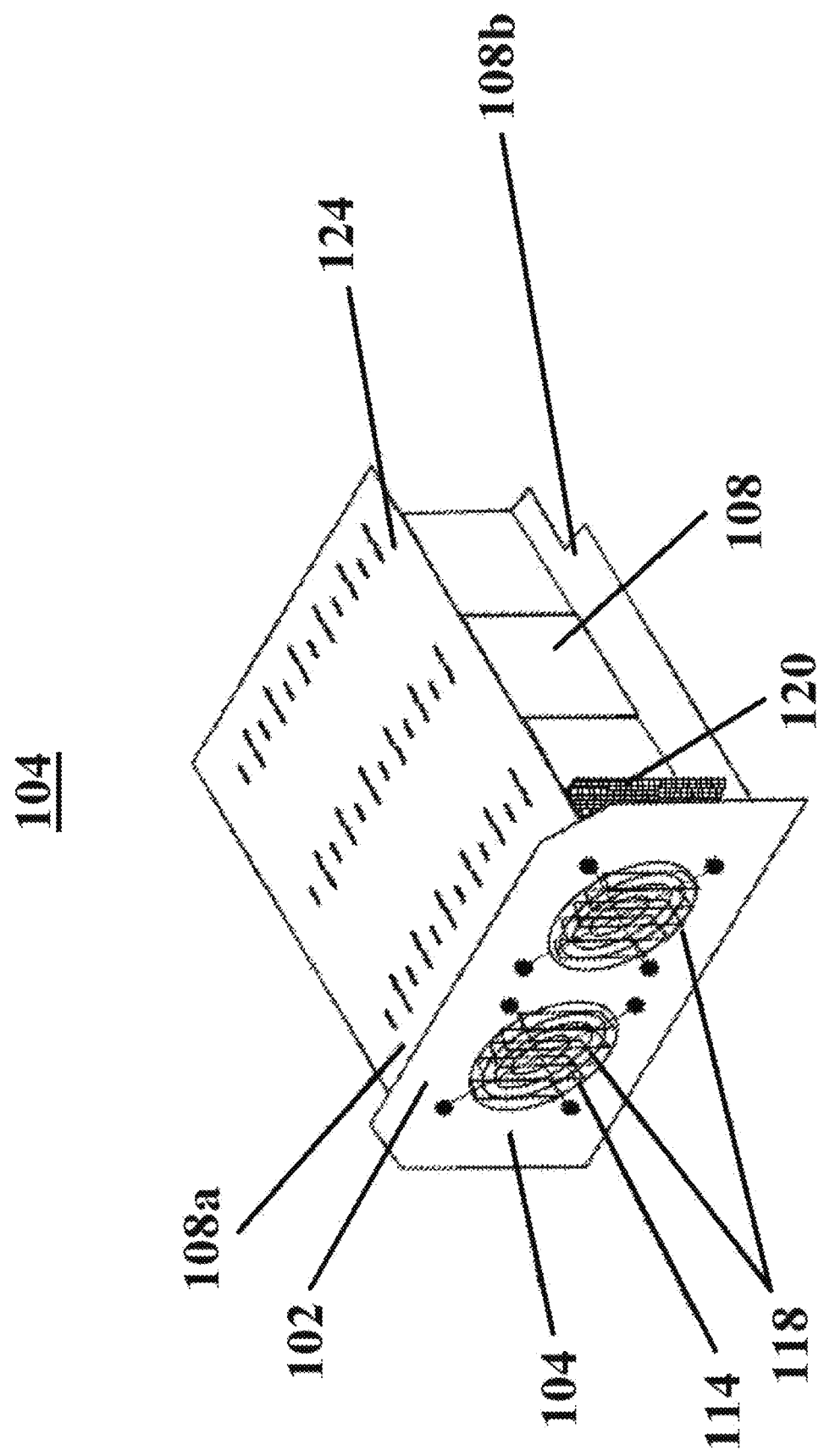

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

In accordance with the present subject matter, to overcome the problems as mentioned above, the present subject matter provides an air decontamination device. The air decontamination device comprises an input unit for receiving air and an output unit for providing decontaminated air. The air decontamination device also comprises a decontamination cassette coupled at a first end to the input unit and coupled at a second end to the output unit. The decontamination unit comprises a plurality of pairs of conducting plates. One conducting plate of each pair is for being positively charged and the other conducting plate of each pair is for being negatively charged. The positively charged plate and negatively charged plate are separated by a distance to form an airflow path. A static electric field is generated in the airflow path between the positively charged conducting plate and the negatively charged conducting plate upon supply of electric power. A three dimensional material is coupled to both sides of each of the conducting plates of the plurality of pairs of conducting plates that comprises surface moieties for imparting microbiocidal activity. The three dimensional material is potentiated by the static electric field in the airflow path to kill microbes present in the air flow path. The microbiocidal property of the three dimensional material is enhanced due to the creation of static electric field.

The air decontamination device provides over a billion-fold drop in microbial count in the output air when compared to the input air. The output air provided by the air decontamination device is cleaner and contains vastly reduced amounts of harmful microbes. The air decontamination device not only traps but also kills the microbes present within the room and achieves a higher decontamination efficiency when compared to conventional air purification devices. Further, as the air passes tangentially with respect to the microbiocidal surface, flow rate of air remains unaffected. There is no or little pressure drop due to the tangential flow of air.

In addition, the air decontamination device of the present subject matter has low requirements of power. This is because the very high electric field is applied across air, which is a very poor conducting medium. Hence, the current generated across the conducting plates is extremely low, resulting in low power requirements. Further, as the microbes are trapped and killed by virtue of their innate charge, power consumption is further reduced. This is due to non-requirement of the particle charging unit of ESPs. The operation of the air decontamination device can also be easily modified by varying the field strength supplied. The air decontamination device may also be fabricated to be portable.

The above-mentioned implementations are further described herein with reference to the accompanying figures. It should be noted that the description and figures relate to exemplary implementations and should not be construed as a limitation to the present subject matter. It is also to be understood that various arrangements may be devised that, although not explicitly described or shown herein, embody the principles of the present subject matter. Moreover, all statements herein reciting principles, aspects, and embodiments of the present subject matter, as well as specific examples, are intended to encompass equivalents thereof.

Figure 1C:
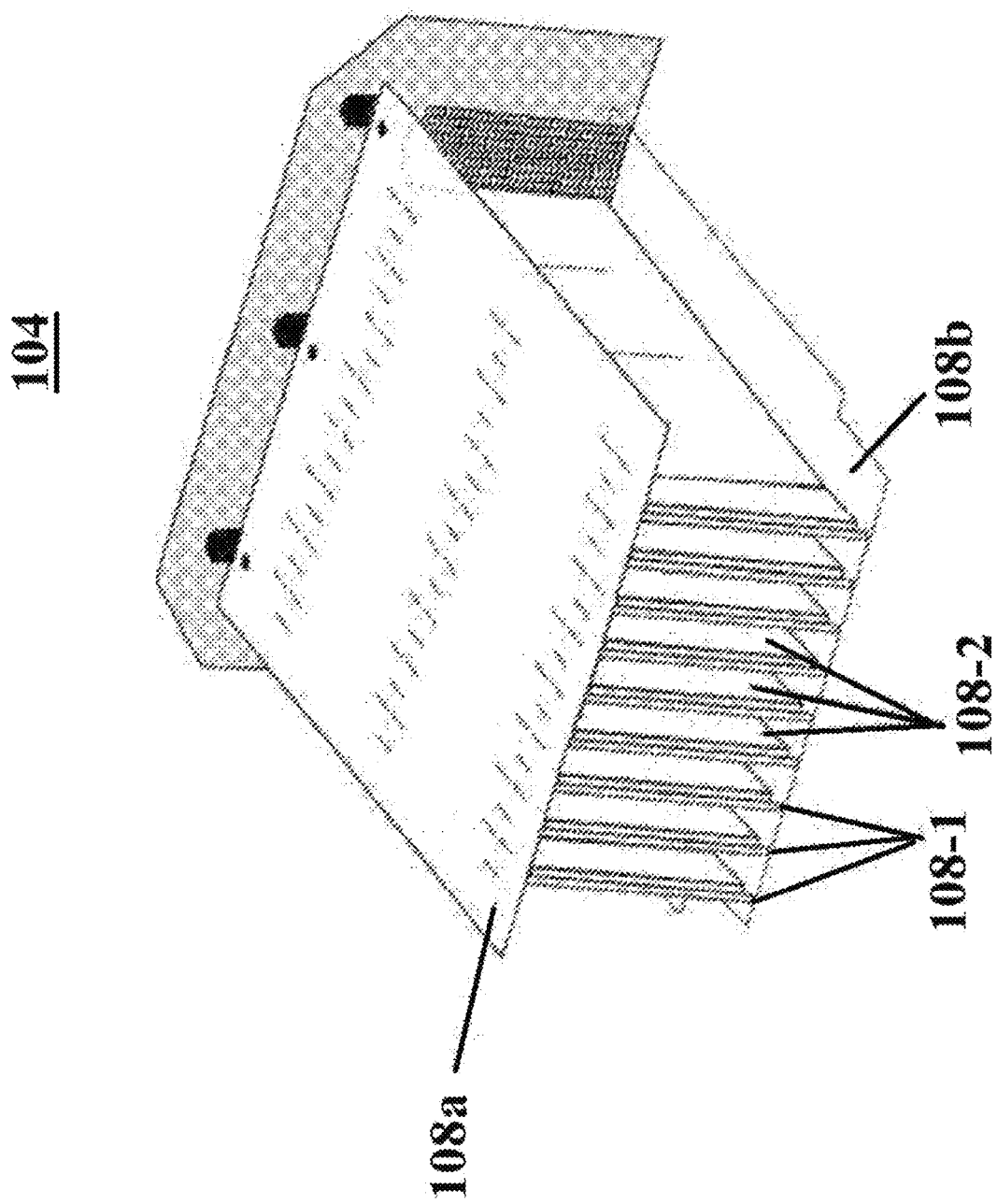

FIG. 1a depicts a general construction of an air decontamination device 100 of the present subject matter, in accordance with an implementation of the present subject matter. The air decontamination device 100 comprises an input unit 102, a decontamination unit 104 that is in the form of a removable cassette, and an output unit 103. The input unit 102 is for receiving air flow and contains inlet vents 114 and the flow out of the decontaminated air 116 passes through output grills 112 on either side of the output unit 103. The output unit 103 is for providing decontaminated air 116. The output unit 103 further comprises a plurality of sensors for sensing temperature, humidity, microbial content, and combinations thereof (not shown in the FIG. 1a) in the decontaminated air. In an implementation, the air decontamination device 100 includes an electronic control unit 126 supported by a microcontroller or a microprocessor configured to increase or decrease rate of delivery of the decontaminated air based on the sensed temperature, humidity, and microbial content. For example, the microprocessor can reduce rate of delivery of decontaminated air if the microbial content in the decontaminated air is expected to be beyond a predetermined threshold. FIG. 1b and FIG. 1c illustrate the construction of the internal decontamination unit cassette 104 that is coupled at a first end 122 to the input unit 102 and coupled at a second end 124 to the output unit 103.

The decontamination unit 104, as shown in the view FIG. 1c comprises a plurality of pairs of conducting plates 108. Each pair of conducting plates 108 comprises a positively charged conducting plate (108-1), and a negatively charged conducting plate (108-2). The positively charged conducting plate (108-1), and the negatively charged conducting plate (108-2) are charged when a static electric field that ranges from 2.7 KiloVolt/centimetre (kV/cm) to 4.2 kV/cm is applied. The plane of the positively charged conducting plate (108-1) is aligned parallel to the plane of the negatively charged conducting plate (108-2) and the positively charged conducting plate (108-1) and the negatively charged conducting plate (108-2) are separated by a distance between 8 mm to 12 mm to form an airflow path (212) inside the decontamination unit (104).

The three dimensional material 110 are coupled to both side of each of the plurality of conducting plates 108 and contains chemical moieties embedded in it. While not shown in the FIG. 1a, the air decontamination device 100 may also comprise a plugging unit to receive power from a power source to provide the source of the voltage needed to set up an electric field between the pairs of conducting plates 108. The air flow needed for the decontamination unit 104 to function may be a ventilating fan (not shown in FIG. 1a) that drives the flow of an input air through the decontamination device 100 to form the air flow path when the decontamination device 100 is used. The input air present in the room may contain particulate matter, such as dust, smoke, dirt, hair, animal dander, and microbes, such as bacteria and fungi. It may be understood that other suction mechanisms may be used in place of the ventilating fan, as will be understood by a person skilled in the art. The sieve 120 may be placed behind the ventilation fan in the device.

The sieve 120 may be a mesh, net, or a metal grill. The sieve 120 has openings of small size that only allow particles with a size of few microns to penetrate. For example, the particles which have size greater than $10^{-2}$ cm are collected by the sieve 120 and the smaller sized particles pass through it to the decontamination unit 104. Therefore, microbes like bacteria and fungi that were present in the input air are pulled into the decontamination unit 104 from the room, while macroparticles are collected by the sieve 120.

FIG. 1b is an illustration of the decontamination cassette 104 from one view angle. Air received by the input unit 102 flows through the decontamination unit 104 through the input vents 114 and input grills 118, and in one implementation through a sieve 120. As the air flows through the decontamination unit 104, the microbes in the air are trapped on the plurality of conducting plates 108 by virtue of their innate Zeta potential charge. The microbes are killed by the potentiated three dimensional material 110 coupled to the plurality of conducting plates 108. Therefore, the air gets decontaminated by virtue of the synergistic effect between static electric field applied between the conducting plates 108 and the three dimensional material 110. The decontaminated air flows out of the output unit 103. Various embodiments of the present subject matter are described herein.

FIG. 1c illustrates the assembly of the plurality of parallel conducting plates 108 with the three dimensional chemical moiety embedded material 110 in the decontamination device cassette 104. The plurality of parallel conducting plates 108 that is coupled to the 3D material, which is capable of acquiring enhanced microbiocidal activity, are held in place between the top and bottom insulating support plates 108a and 108b respectively. The insulated support plates (108a, 108b) support and hold the plurality of pairs of conducting plates (108-1 and 108-2 pairs) in position. The electrical potential to the plurality of conducting plates (108) is fed through the top and bottom assemblies 108a and 108b respectively with one used for routing the positive potential and the other for the negative potential when the DC voltage is used. When using AC voltage, this positive and negative discrimination is not there for the connections.

Figure 1D:
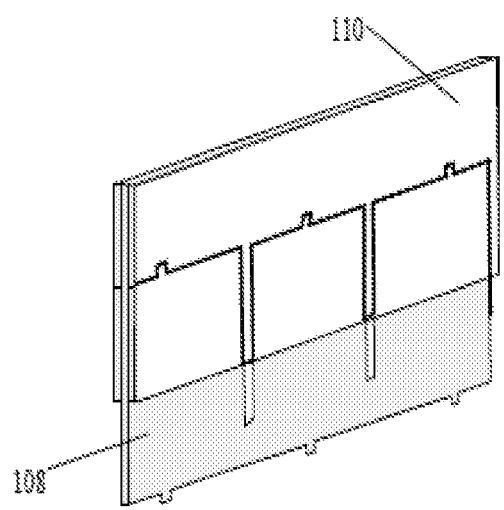

FIG. 1d illustrates a three dimensional microbiocidal material 110 coupled to both sides of one of a plurality of conducting plates 108, in accordance with an implementation of the present subject matter. In another implementation, each pair of the parallel conducting plates includes a composite material comprising multiple layers. Each layer of the multiple layers comprises surface moieties cross-linked with a microbiocidal agent. The fabric and the composite material can be coupled to the plurality of pairs of conducting plates 108 by using adhesives, clips, or any other method known in the art.

Three-dimensional (3D) fabric (i.e. the microbiocidal material 110) is known to persons skilled in the art. 3D fabrics are fabrics which comprise multiple layers. In another implementation, the microbiocidal material 110 can be a two-dimensional fabric comprising a single layer of fabric. In yet another implementation, the microbiocidal material 110 has more than one layer of a suitable 2D fabric and preferably three layers, each having a predetermined thickness and a plurality of apertures.

In each of the above mentioned microbiocidal fabric implementations, the microbiocidal material 110 contains surface moieties that impart microbiocidal activity to the surface in the presence of an electric field. The surface allows binding of a chemical agent to impart microbiocidal activity. In an implementation, the chemical agent is selected from the group comprising bactericides, fungicides, quaternary ammonium salts, such as 3-(trimethoxysilyl) propyl-N-octadecyl-N,N-dimethyl ammonium chloride, 3-(trimethoxysilyl)propyl-N-tetradecyl-N,N-dimethyl ammonium chloride, 3-(trimethoxysilyl) propyl-N,N-didecyl-N-methyl ammonium chloride, 3-(trihydroxysilyl) propyl-N-octadecyl-N,N-dimethyl ammonium chloride.

In another implementation, the microbiocidal material 110 is the fabric comprising the microbiocidal agent impregnated on the fabric. In an embodiment, the microbiocidal agent is a composite material comprising multiple layers. Each layer of the multiple layers comprises surface moieties cross-linked with a potential microbiocidal agent. The fabric and the composite material can be coupled to the plurality of pairs of conducting plates 108 by using adhesives, clips, or any other method known in the art.

Figure 2A:
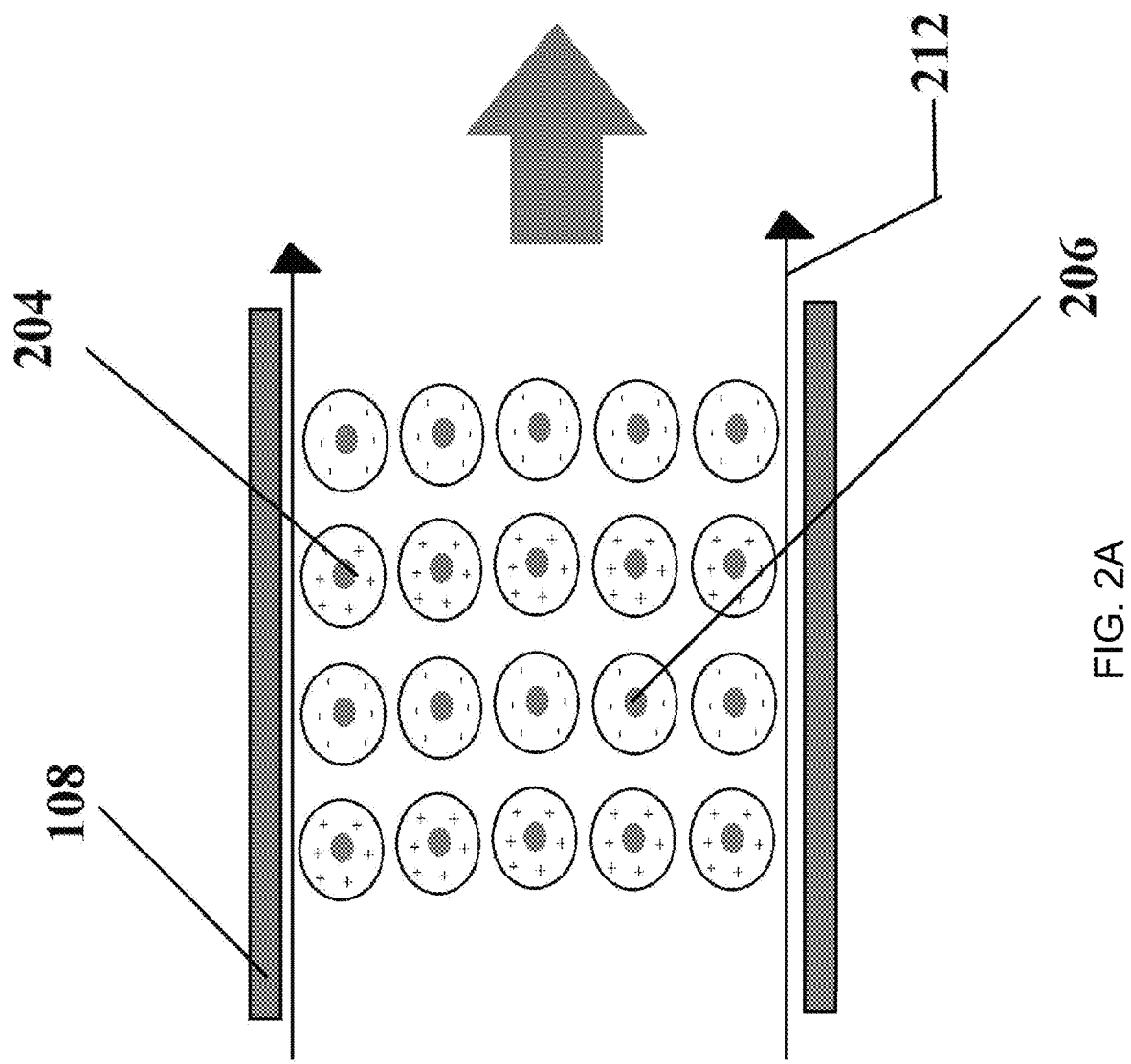
FIGS. 2a and 2b illustrate a working principle of the air decontamination device, in accordance with an implementation of the present subject matter.
Figure 2B:
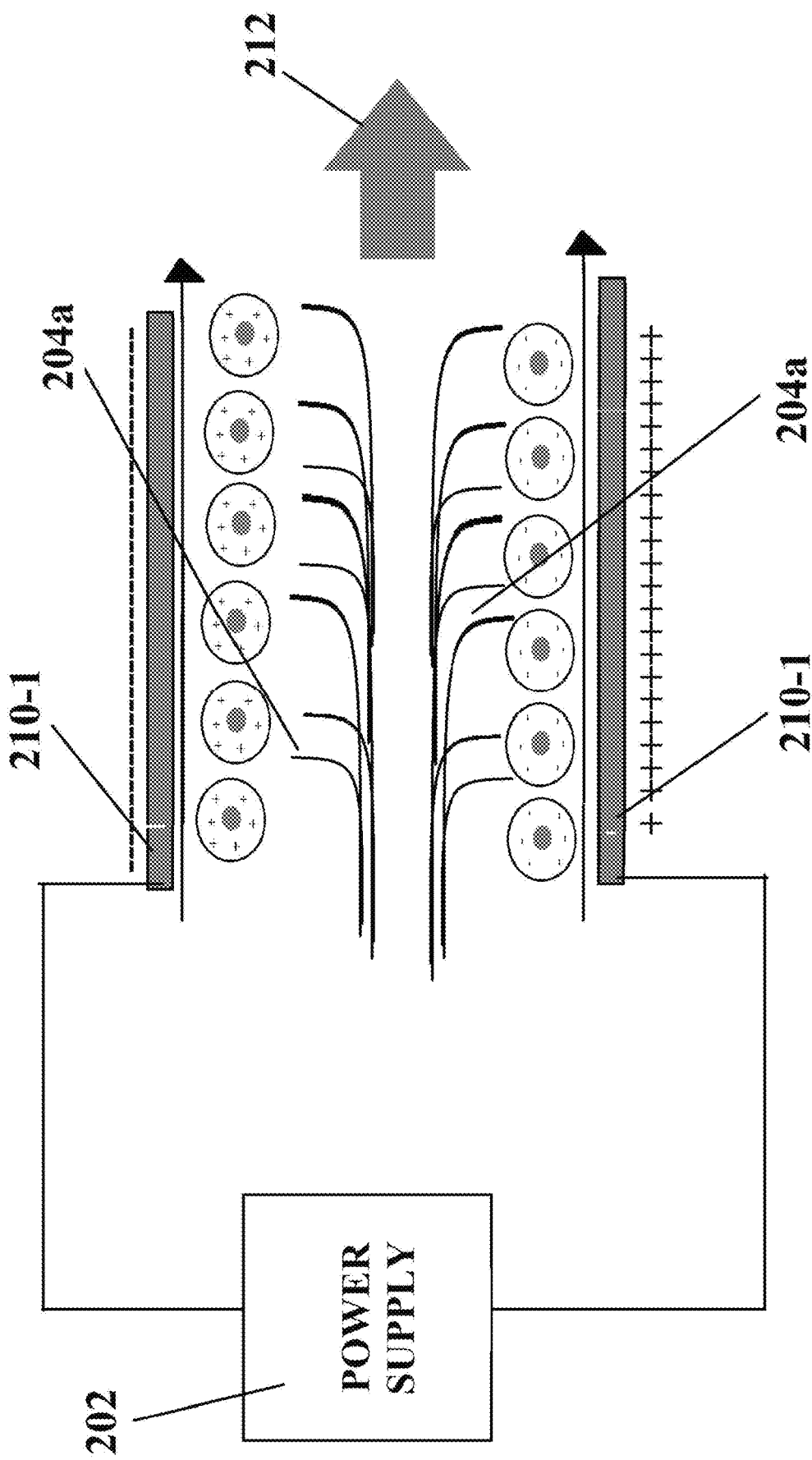

FIGS. 2a and 2b illustrate the dynamics of the air flow path with respect to the zeta potential charged microbes that may be in the air flow path and need to be decontaminated. The plurality of pairs of conducting plates 108 with their respective three dimensional microbiocidal agent coated fabric 210-1 are arranged such that their length forms the airflow path 212. The length of the conducting plate 108 is proportional to the contact time between the air flowing in the airflow path 212 and the plurality of pairs of conducting plates 108 with their respective three dimensional microbiocidal agent coated fabric 210-1. As will be understood by a person skilled in the art, the length of the plurality of pairs of conducting plates 108 with their respective three dimensional microbiocidal agent coated fabric 210-1 depends on flow rate of air through the airflow path 212. For example, the length of each of the plurality of pairs of conducting plates 108 with their respective three dimensional microbiocidal agent coated fabric 210 increases with increase in flow rate of air to increase contact time between the air flowing in the airflow path 212.

Air for purification is received into the decontamination unit 104 from the air input unit 102 (as shown in FIG. 2a) and flows through the airflow path 212 in the direction 208 that is parallel to the conducting plates. 204 and 206 illustrate the positively and negatively charged microbial particles that may be the contamination on the flowing air. In the absence of an electric field as illustrated in FIG. 2a, the microbial cells that touch the chemical moiety coated three dimensional fabric 210-1 are structurally destabilized but not killed by the action of the chemical moieties in the three dimensional material 201-1. Microbes that do not touch the surface 201-1 are not killed. The killing potential of the three dimensional material with the chemical moieties is thus limited, and a consequence of the inherent, weak, microbiocidal nature of the chemical moieties on the surface 201-1.

FIG. 2b illustrates the action due to the introduction of a static electric field using a power supply 202. The power supply/source 202 creates a static electric field between the chemical moiety coated three dimensional fabric 210-1 that are coupled to the positively and negatively charged conducting plates. This electric field being perpendicular to the air flow direction 212, creates a force on the zeta potential charged microbes 204 and 206. The field is thus able to provide a lateral force to move the respective microbes to either of the charged chemical moiety coated three dimensional material 210-1 that are coupled to the positively and negatively charged conducting plates. The power source 202 is so constructed that the voltage provided is between 2 to 5 kV and a gap between the chemical moiety coated three dimensional fabric 210-1 coupled to the positive and negative charged plates is adjusted between 8 mm to 12 mm so that the electric field is between 1 kV/cm to 5 kV/cm.

As air flows through the airflow path 212, microbes in the air are propelled to the plurality of chemical moiety coated three dimensional fabric 210-1 that are coupled to the positively and negatively charged conducting plates 108. For example, the positively charged microbial particles and the negatively charged microbial particles are attracted towards oppositely charged conducting plates 108. The arrow 204a indicates the attraction of the charged microbial particles towards the plurality of pairs of conducting plates 108. The microbes, therefore, get trapped and deposited on the plurality of chemical moiety coated three dimensional fabric 210-1 that are coupled to the positively and negatively charged conducting plates 108. The deposited microbes are then killed by the potentiated microbiocidal material 210-1.

The electrical power source 202 is selected from one of an AC power source of frequency 50 Hz to 1 kHz, DC power source, and a pulsed power source. In an implementation, the plurality of pairs of conducting plates 108 are connected to the electrical power source 202 of 1-5 kV. In an implementation, the plurality of pairs of conducting plates 108 are connected to a pulsed power source with having 5-50% duty cycle, frequency of 1-30 kHz and amplitude of 1-5 kV. In an implementation, the plurality of conducting plates 108 is connected to DC power source of 1 to 5 kV. In another implementation, the plurality of conducting plates 108 is connected to AC power source of 1 kV to 5 kV.

Figure 3A:
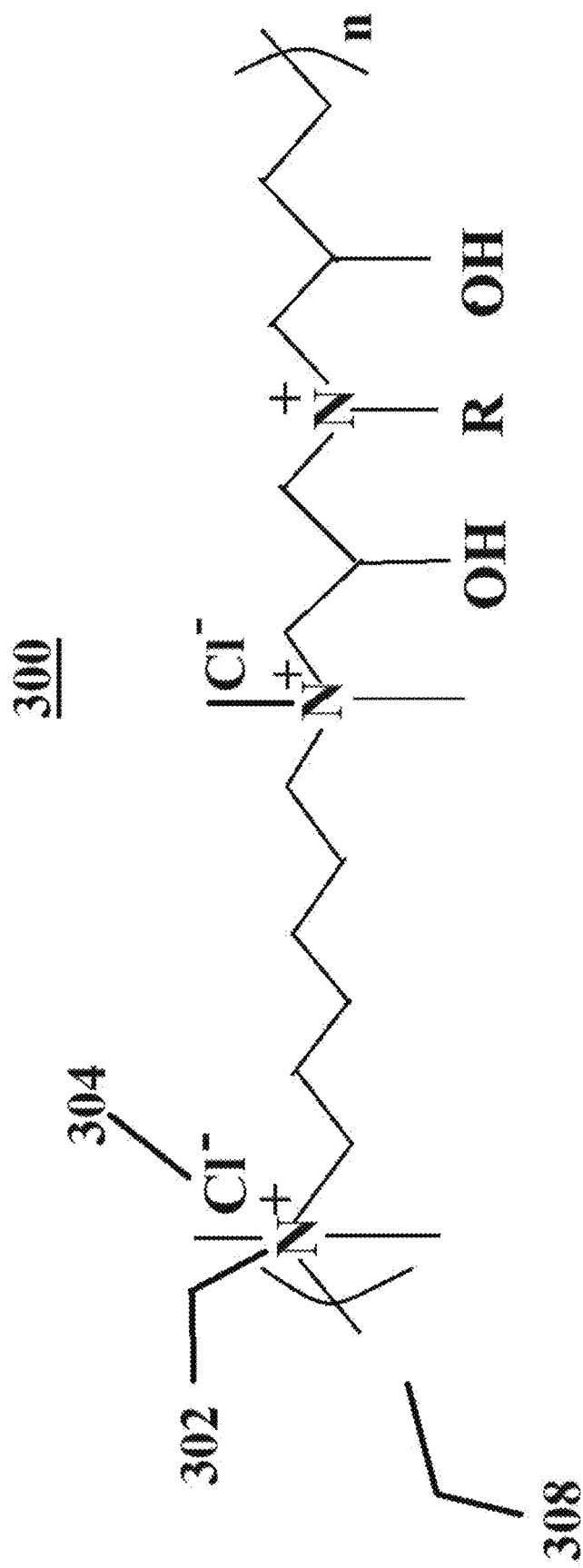
FIGS. 3a to 3c illustrate a modification of the alignment of chemical moieties embedded in the three dimensional material coupled to the electrically charged conducting plates of the air decontamination device in accordance with an implementation of the present subject matter.
Figure 3B:
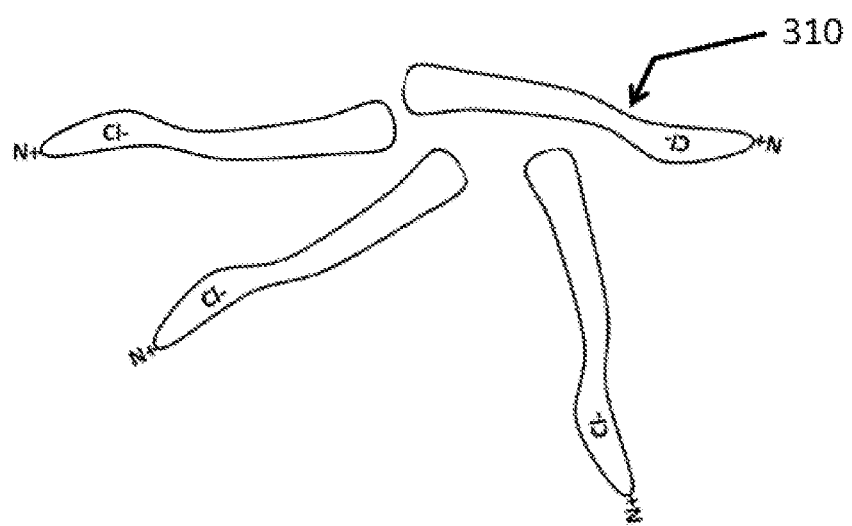
Figure 3C:
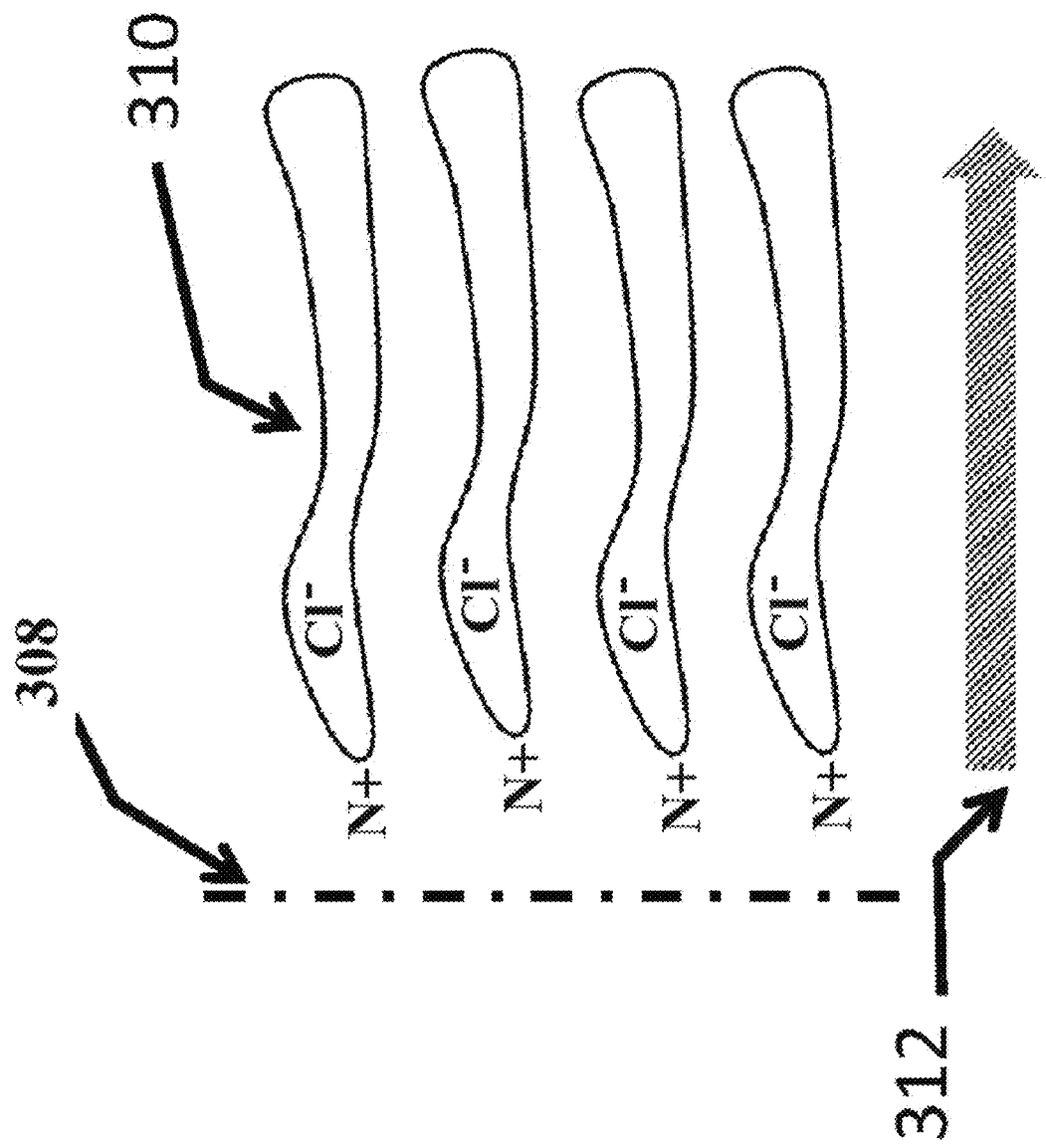

FIG. 3a to FIG. 3c illustrate the modified physical disposition of the chemical moiety 300 used to coat the three dimensional fabric 210-1 that is coupled to the positively and negatively charged conducting plates 108. The nature of all possible moieties used for microbiocidal activity as illustrated in the FIG. 3a are known in art. These moieties, as illustrated in FIG. 3a contain a long chain organic chemical structure with the positive charge associated with the terminal element which is an ammonium entity 302 (N+) and balanced by a corresponding negative charge 304 (in this case a Cl ion) held in rest of the structure. The weak microbiocidal activity of this class of moieties, as known in the art, is attributed to the positive charge associated with the terminal element of the ammonium entity 302 and its ability to create a damage in the microbial surface membrane 308 when a microbe membrane surface comes in contact with the terminal end 304 of the chemical moiety 300. The nature of this microbiocidal interaction and the kill involves charge transfer between the ammonium entity 302 and the surface membrane of the microbe 308. The charge transfer to the microbial membrane damages its structural integrity and over time, leads to the death of the microbial cell.

The interaction of the applied static electric field and the potentiation of the chemical moieties is further illustrated in FIG. 3b and FIG. 3c. The illustration in FIG. 3b shows the random alignment of the chemical moieties 300 bonded to the individual threads of the 3-D fabric (not shown in the illustrations FIG. 3b and FIG. 3c) which is treated with this chemical moiety. FIG. 3c shows the realignment of the moieties 300 to the direction of the electric field 312. The strong static electric filed ensures that the large concentration of the surface moieties based on a per square cm area, equivalent area or any other area units is forced to become unidirectional throughout the depth of the three dimensional fabric that is treated with this chemical moiety 300. When the static electric field is strong enough, the net alignment of all the moieties 300 distributed in the three dimensional fabric is parallel to one another and perpendicular to the plane 310 in which the air and the microbial cells flow. Beyond a threshold all the treated moieties distributed in the flexible three dimensional fabric structure are aligned in the direction of the electric field and thus there is an electric field value depending on the structure of the three dimensional fabric that ensures that beyond the threshold the alignment as illustrated in FIG. 3c is complete. This complete alignment is facilitated by the reason that the structure of the moiety 300 constitutes an electrical dipole and so a strong electric field would give directional alignment to the electrical dipoles. The microbiocidal activity of these aligned dipole moieties presents enhanced activity with the plane 310 of the aligned terminal end charges 300 which are parallel to the electric field and perpendicular to the plane 310.

Further, since the kill happens on one to one basis between the microbe cell membrane 308 and the positive charge 302, the summation of these kills by a collection of these moieties as aligned in FIG. 3c has a non-zero energy requirement on a continuous time basis. The electric field helps with a continuous charge transfer and this charge replenishment mechanism is essentially proportional to the charge concentration on square area basis on the three dimensional treated fabric. It is to be noted that the currents that are connected with these charge transfers on a continuous basis are very small and in the uA to nA ranges and so not measurable since these charge transfers are at the molecular level. Thus, while it is essential that the voltage to create the electric filed is to between 1 kV to 5 kV, the wattage requirement is limited to a few watts.

The fundamental design of the decontamination device 100 ensures that the aligned structure in FIG. 3c is enabled and can be presented to a path of air that is to be decontaminated of the microbial load.

Figure 4:
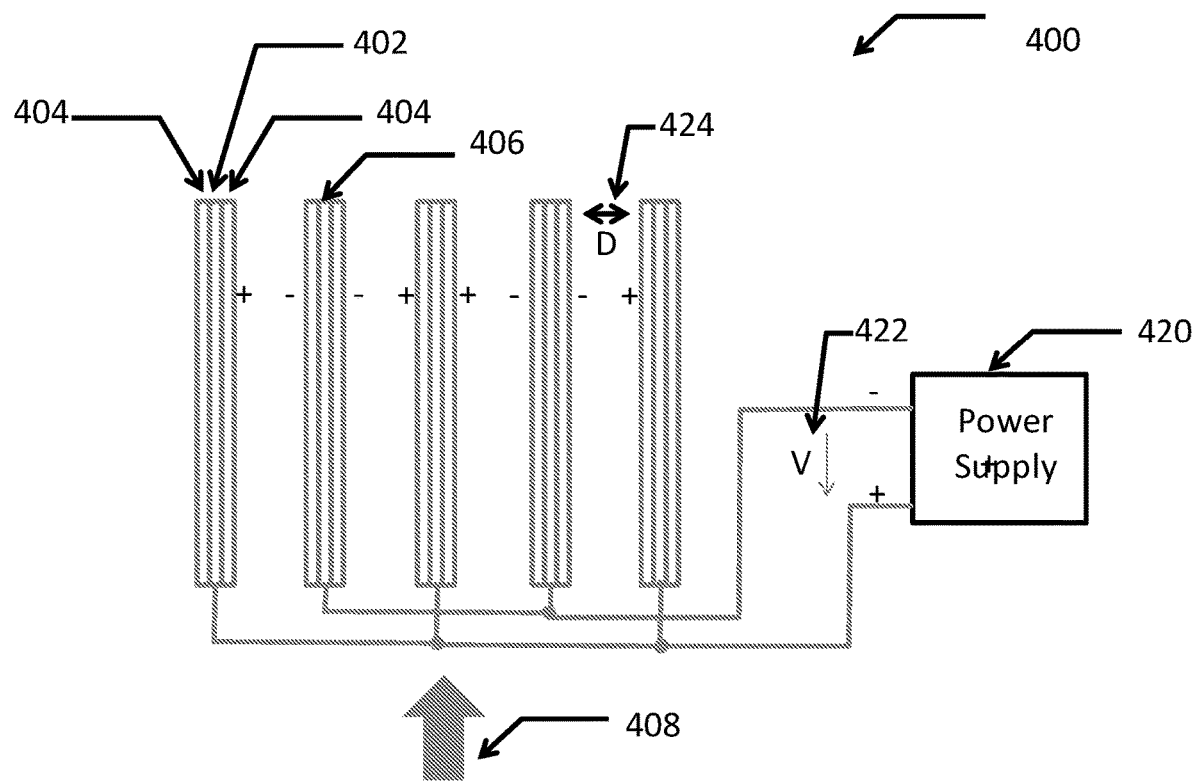
FIG. 4 illustrates a lateral cross-section of airflow path between the pairs of conducting plates in accordance with an implementation of the present subject matter.

This basic construct is illustrated in FIG. 4 where a set of parallel conducting electrodes 402 (positive plate) and 406 (negative plate) form an air flow path and the electric field is perpendicular to the air flow path. The three dimensional chemical moiety coated fabric/material 404 has the charged moieties and is coupled to either side of electrical conducting electrodes 402 that constitute the electrical conducting plates which form the electric field. The air that is possibly contaminated with a microbial load is made to flow in the direction 408 parallel to the conducting plates (402 and 406) and the coated three dimensional fabric 404 coupled to the electrode set or the conducting plates (402 and 406).

The power supply 410 creates a static electric field by generating a high voltage in the range of 1 kV to 5 kV and the power supply 410 is suitably protected for overload due to inadvertent arcs that potentially occur in the electrical field electrodes when the high voltage is used. The operating range of the electrical field is characterized by the applied voltage 412 and the inter-electrode distance 414, and is of electrical field strength V/D. The design ensures that the electrical field strength does not result in a high field discharge and a consequent arc and so the voltage is limited to a maximum of about 5 kV and the inter-electrode distance 414 held between 0.8 cm to 1.2 cm and thus limiting the maximum electric field to 5 kV per cm.

Since, the live microbes have charged membrane surfaces, the electric field that is perpendicular to the air flow path 408 forces the charged microbe to move perpendicular to the flow path and thus move towards the electrode plates formed by 402 and 406 that are coupled to the three dimensional treated fabric 404, and once the microbes are trapped in the three dimensional treated fabric 404 by this field, they get killed by the aligned moieties in the three dimensional fabric as illustrated and explained with respect to FIG. 3a to FIG. 3c above.

The present subject matter will now be illustrated with working examples, which are intended to illustrate the working of disclosure and not intended to be taken restrictively to imply any limitations on the scope of the present disclosure. Unless defined otherwise, all technical and scientific terms used herein have the same meaning as commonly understood to one of ordinary skill in the art to which this disclosure belongs. It is to be understood that this disclosure is not limited to the particular methods and experimental conditions described, as such methods and conditions may vary depending on the process and inputs used as will be easily understood by a person skilled in the art.

EXAMPLES

Example 1: Study of the Effect of Electric Field on Material 110

Figure 5:
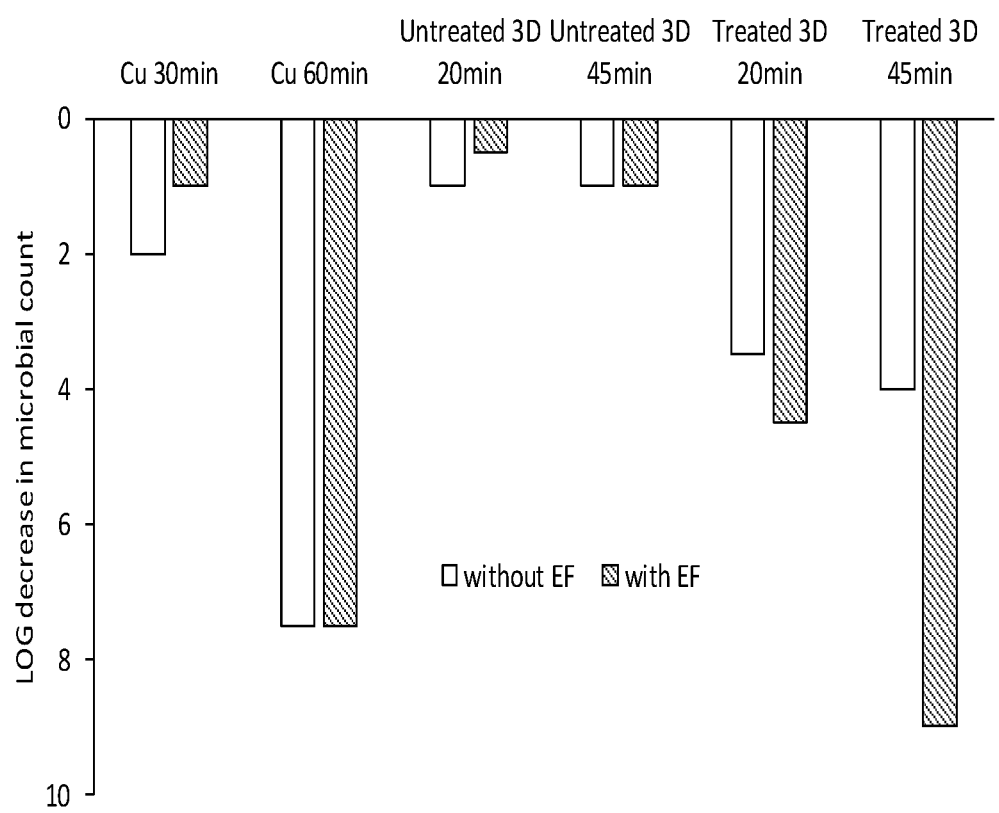
FIG. 5 depicts a graphical plot of the enhanced microbial kill characteristics reached with the air decontamination device in accordance with an implementation of the present subject matter.

In this example, as illustrated by the graph in FIG. 5, the greatly enhanced effect of the electric field on material 110 in a decontamination process was studied. *Escherichia coli* K12 with pET28a plasmid bearing kanamycin resistance gene was grown in Luria-Bertani (LB) broth containing 30 μg/ml of kanamycin at 37° C. Known number of *E. coli* was spotted onto three different kinds of 2 cm² sized surfaces, namely samples of the three-dimensional fabric with the chemical/potentially microbiocidal agent (110), three-dimensional fabric without any chemical agent and copper. The known number of *E. coli* was obtained by diluting the LB broth in sterile 1×PBS and plating it to enumerate the total number of bacterial particles present in the solution.

The study was conducted using the following conditions: in a first condition, the decontamination effect was studied for 30 min and 60 min in the presence of the microbiocidal agent Copper and by the application or not of a 2 kV/cm electric field (represented by the graphs of Cu 60 min and Cu 30 min in FIG. 5). In a second condition, the decontamination effect was studied in the presence of the untreated three dimensional fabric and in the absence and presence of electric field of magnitude 2 kV/cm (represented by the graphs of untreated 20 min and untreated 45 min in FIG. 5); in a third condition, the decontamination effect was studied with the use of the chemical moiety coated material 110 in the absence and presence of an electric field of magnitude 2 kV/cm.

FIG. 5 further shows that copper surfaces at 60 minutes had excellent microbiocidal activity on bacteria applied to the surface, with microbial count reducing by ~7 logs. However, this microbiocidal activity was not enhanced by the application of electric fields. The application of electric fields for 20 minutes and 45 minutes on three dimensional fabric that was not treated with the chemical moiety (e.g. the chemical moiety 300) did not impact microbiocidal properties to the fabric surface. A kill of ~1 log was observed, that is close to the error associated with the method used to enumerate bacterial colonies. The three dimensional surface coated with the chemical moiety alone was potentiated by the application of the electric field. Application of a 2 kV/cm electric field for 45 minutes enhances the ability of the surface to kill over a billion microbes.

Figure 6:
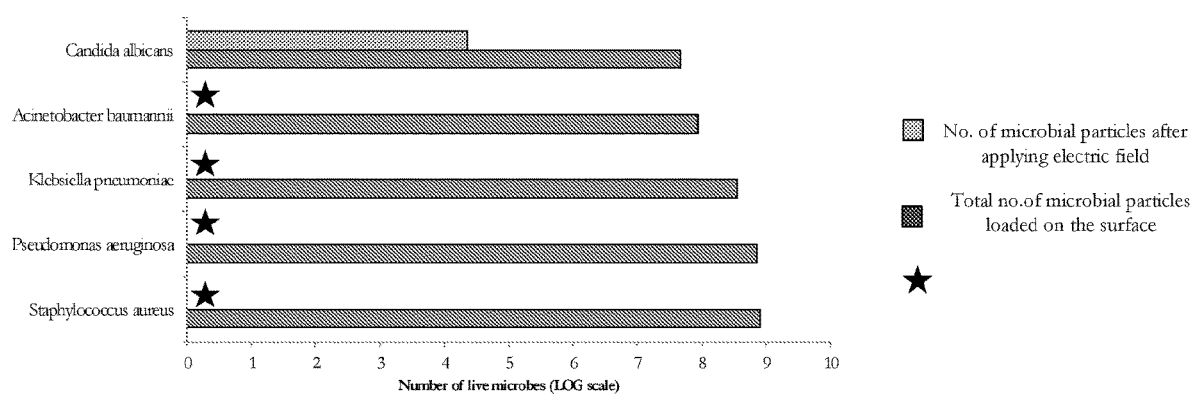
FIG. 6 depicts a graphical plot of the enhanced kill characteristics reached for different types of microbes with the air decontamination device in accordance with an implementation of the present subject matter.

In this example, as illustrated by the graph in FIG. 5, the greatly enhanced effect of the electric field on 3D material 110 in a decontamination process was studied Further, studies were conducted in the following Example-2 to examine the enhanced ability of the electric field potentiated 3D material 110 to kill other microbes, as illustrated in the graph of FIG. 6, namely *Candida Albicans, Staphylococcus aureus, Pseudomonas aeruginosa, Klebsiella pneumoniae,* and *Acinetobacter baumanii.*

Example 2: Study of Enhanced Killing Ability of Three Dimensional Material 110 on Other Microbes

*Staphylococcus aureus, Pseudomonas aeruginosa, Klebsiella pneumonia, Acinetobacter baumanii* and *Candida albicans* were grown in LB broth at 37° C. Known amounts of microbial population were spotted onto two samples of the three-dimensional fabric with the chemical agent (e.g. potential microbiocidal agent). The known number of microbes was noted down for each microbe to indicate the initial number of viable microbes impregnated on the two samples.

To test the effectiveness of decontamination in the absence of electric field, one sample of the three-dimensional microbiocidal fabric was kept in a sterile environment for 1 hour. The three-dimensional fabric was resuspended in 10 ml of sterile 1×PBS, diluted accordingly and plated on LB agar. The plates were incubated at 37° C. for 16 hours. Individual colonies were observed after the incubation period, which were used to enumerate the total number of viable bacterial particles present in the suspension obtained from the three-dimensional fabric which was not exposed to electric field.

To test the ability of electric fields to potentiate the microbiocidal ability of three dimensional fabric 110, the other three-dimensional fabric sample was sandwiched between two conducting plates 108. The conducting plates 108 were then coupled to the electrical power source 410. An electric field of 1.5 kV/cm was applied across the sandwich for one hour. At the end of one hour, the three-dimensional fabric was taken out and residual live microbes estimated.

FIG. 6 depicts the ability of the electric field potentiated three dimensional surface to kill various bacteria and a fungus. As can be seen, no live bacteria were observed after 1 hour of the trial (shown by stars to denote microbial count was below the limit of detection).

Example 3: Effect of Increasing Electric Held Strength in Reducing Airborne Bacterial Load The effect of increasing electric field strength was studied in the embodiment of the air decontamination device 100.

*Escherichia coli* K12 with pET28a plasmid bearing kanamycin resistance gene was grown in LB broth containing 30 µg/ml of kanamycin at 37° C. Known amount of *Escherichia coli* K12 with pET28a plasmid bearing kanamycin resistance gene were taken in a 6-jet Collision nebulizer. The nebulizer was connected to a test chamber of 3'*3'*3' dimension that contained the decontamination device 100. The test chamber is a transparent chamber which is completely sealed except for ports to introduce nebulized bacteria and to sample the air in the chamber.

Bioaerosols were generated from this 6-jet nebulizer in the test chamber. Immediately after the nebulization process, sampling of the test chamber was done by pumping air from the test chamber into sterile 1× PBS (100 ml) of known volume for a known period of time (2 minutes). This provided the initial number of viable bacteria floating in air.

To study the effect of increasing electric field strength, conducting plates 108 coupled to three dimensional fabric without the chemical agent, conducting plates 108 coupled to three-dimensional fabric with the chemical agent, and conducting plates 108 coated with copper were taken in three air decontamination devices 100. The said three air decontamination devices 100 were placed in individual test chambers comprising the bioaerosols. The air decontamination devices 100 were operated for 30 minutes at various magnitudes of electric field. At the end of 30 minutes, the decontamination devices 100 were turned off; and air in the test chamber was sampled by collecting in sterile 1× PBS buffer solution for a limited time using a vacuum pump.

Figure 7:
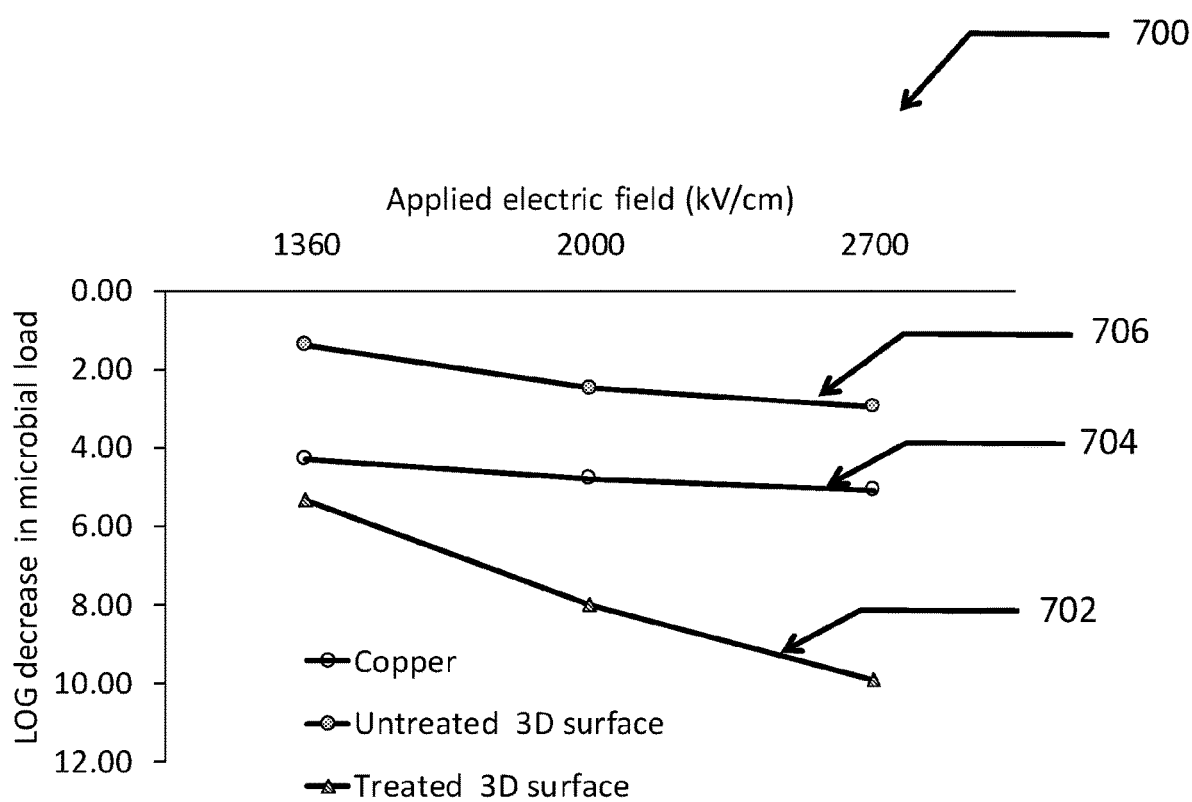
FIG. 7 depicts synergistic and enhanced effect of static electric field and the three dimensional material in killing of bacteria, in accordance with an implementation of the present subject matter.

The effect of increasing electric field strength on bacterial load reduction is also shown in FIG. 7. As can be seen, bacterial kill increases with increasing electric field strength only when the electric field is supplied to decontamination devices 100 containing three dimensional fabric coated with chemical agent (i.e. potential microbiocidal agent). At the end of thirty minutes, application of 2.7 kV to the decontamination device 100 where the conducting plates 108 were coupled to the three-dimensional fabric 110 bearing the chemical agent reduced the bacterial load in the chamber by over a billion-fold. When the conducting plates 108 were coupled to the three-dimensional fabric without the chemical agent, or were coated with copper, microbial kill was not enhanced by the application of electric fields of increasing electric field strength.

In conclusion the increasing strength of static electric field improves the microbiocidal activity of the decontamination device 100 constructed with electrode surfaces that are bonded to the specific chemical moiety in a logarithmic fashion. Increasing electric field strength did not improve the microbiocidal activity of devices constructed with electrodes coated with known microbiocidal agent copper; or induce microbiocidal activity in decontamination devices 100 constructed with composite electrodes coupled to untreated fabric.

Figure 8:
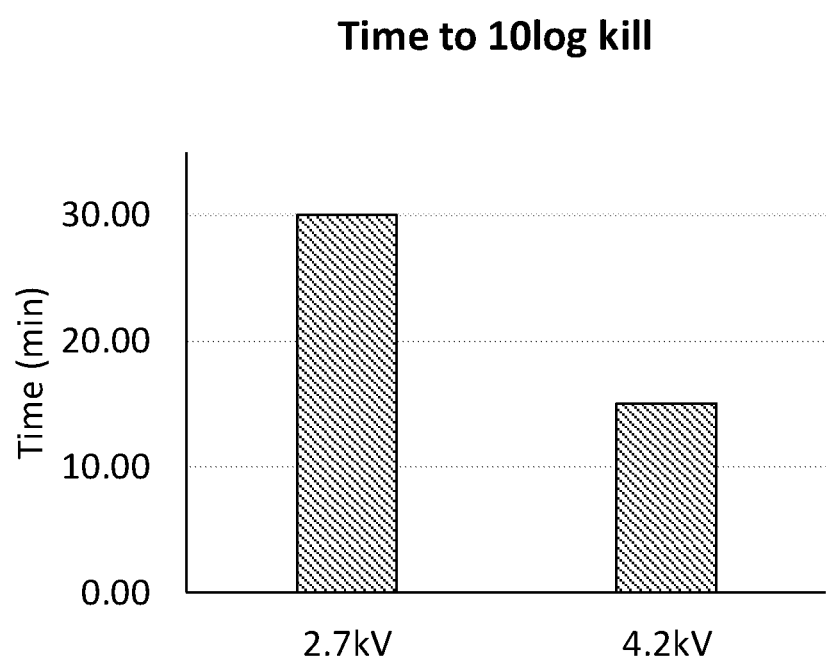
FIG. 8 depicts a time taken for the killing of $10^{10}$ bacteria achieved with static electric field of 2.7 kV/cm and 4.2 kV/cm in accordance with an implementation of the present subject matter.

FIG. 8 further shows that the same billion fold reduction that is obtained by the application of 2.7 kV/cm for 30 minutes in the air decontamination device 100 can be achieved by the application of 4.2 kV/cm for 15 minutes. Therefore, the air decontamination device 100 provides a significant amount of reduction in the microbes present in the air. The air decontamination device 100 also has low power consumption and therefore can be provided in all zones of hospitals, storage and manufacturing units, culture rooms and chambers, and the like.

FIG. 9 Illustrates a method of applying static electric field to the air decontamination device (100) of FIG. 1 to kill microbial cells and to reduce a level of microbial cell by a billion fold, in accordance with the present subject matter. At step 902, the input unit (102) receives air from environment through a plurality of air inlet vents (114). At step 904, the positively charged conducting plate (108-1) and the negatively charged conducting plate (108-2) are separated by a distance that ranges between 8 mm to 12 mm to form an airflow path (212) inside the decontamination unit (104). At step 906, the three dimensional (3D) material (110) is coupled to both surfaces of each of the positively charged conducting plate (108-1) and the negatively charged conducting plate (108-2). The three dimensional material (110) comprises surface moieties for imparting microbiocidal activity to both surfaces of the positively charged conducting plate (108-1) and the negatively charged plate (108-2). At step 908, the static electric field in the range of 2.7 KiloVolt/centimetre (KV/cm) to 4.2 KV/cm is applied for 15 minutes to 30 minutes, to functionally exert a force on the charged microbial cells present in the air and trap the oppositely charged microbials cells, on the positively charged conducting plate (108-1) and the negatively charged conducting plate (108-2), due to attraction between charges of the microbial cells and the charges of positively charged conducting plate (108-1) and the negatively charged conducting plate (108-2), and enhance the surface moieties dipole of the three dimensional microbiocidal material (110) to complete realignment to a direction of the static electric field to potentiate the microbial activity of the three dimensional material (110) to kill the microbial cells that are trapped or deposited on the positively charged conducting plate (108-1) and the negatively charged conducting plate (108-2) and to reduce a level of the microbial cells inside the decontamination unit (104) by over a billion fold.

Although the subject matter has been described in considerable detail with reference to certain examples and implementations thereof, other implementations are possible. As such, the scope of the present subject matter should not be limited to the description of the preferred examples and implementations contained therein.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments.

We claim:

1. An air decontamination device (100), comprising:
an input unit (102) for receiving air from environment through a plurality of air inlet vents (114);
an output unit (103) for providing decontaminated air;
characterized in that, the air decontamination device (100) comprises:
a decontamination cassette (104) that comprises
a first end (122) that is adapted to couple with the input unit (102), a second end (124) that is adapted to couple with the output unit (103);
a plurality of pairs of conducting plates (108), wherein each pair of conducting plates comprises, a positively charged conducting plate (108-1), and a negatively charged conducting plate (108-2), wherein the positively charged conducting plate (108-1), and the negatively charged conducting plate (108-2) are charged when a static electric field that ranges from 2.7 KiloVolt/centimetre (kV/cm) to 4.2 kV/cm is applied, wherein the plane of the positively charged conducting plate (108-1) is aligned parallel to the plane of the negatively charged conducting plate (108-2), wherein the positively charged conducting plate (108-1) and the negatively charged conducting plate (108-2) are separated by a distance that ranges between 8 mm to 12 mm to form an airflow path (212) inside the decontamination unit (104); and a three dimensional (3D) material (110) that is coupled to both surfaces of each of the positively charged conducting plate (108-1) and the negatively charged conducting plate (108-2), wherein the three dimensional material (110) comprises surface moieties for imparting microbiocidal activity to both surfaces of the positively charged conducting plate (108-1) and the negatively charged plate (108-2), wherein the static electric field in the range of 2.7 KiloVolt/centimetre (KV/cm) to 4.2 KV/cm is applied for 15 minutes to 30 minutes, to functionally exert a force on the charged microbial cells present in the air and trap the oppositely charged microbials cells, on the positively charged conducting plate (108-1) and the negatively charged conducting plate (108-2), due to attraction between charges of the microbial cells and the charges of positively charged conducting plate (108-1) and the negatively charged conducting plate (108-2), and enhance the surface moieties dipole of the three dimensional microbiocidal material (110) to complete realignment to a direction of the static electric field to potentiate the microbiocidal activity of the three dimensional material (110) to kill the microbial cells that are trapped or deposited on the positively charged conducting plate (108-1) and the negatively charged conducting plate (108-2) and to reduce a level of the microbial cells inside the decontamination unit (104) by over a billion fold.

2. The air decontamination device (100) as claimed in claim 1, wherein a sieve 120 is provided between the input unit (102) and the decontamination unit (104), wherein the sieve 120 allows particles have a size less than $10^{-2}$ centimetre (cm) inside the decontamination unit (104).

3. The air decontamination device (100) as claimed in claim 1, wherein the input unit (102) and the output unit (103) comprise a ventilation fan unit, and wherein the decontamination unit comprises insulated support plates (108a, 108b) to support and hold the plurality of pairs of conducting plates (108) in position.

4. The air decontamination device (100) as claimed in claim 1, wherein the output unit (103) comprises a plurality of sensors for sensing temperature, humidity, microbial content in the decontaminated air, wherein the air decontamination device (100) comprises a micro-controller (126) to increase or decrease a rate of delivery of the decontaminated air based on the sensed data of temperature, humidity, microbial content.

5. The air decontamination device (100) as claimed in claim 1, wherein each of the plurality of pairs of conducting plates (108) is connected to an electrical power source (202), wherein the electrical power source (202) is configured to provide the electric field between each pair of conducting plate (108) in the range of 1000 volt per centimetre (V/cm) to 5000 V/cm.

6. The air decontamination device (100) as claimed in claim 5, wherein the electrical power source (202) is selected from one of a DC power source, AC power source, and pulsed power source.

7. The air decontamination device (100) as claimed in claim 6, wherein the AC power source has a frequency in a range of 50 Hertz (Hz) to 1000 Hz.

8. The air decontamination device (100) as claimed in claim 6, wherein the pulsed power source has 5-50% duty cycle, frequency of 1 kilo Hertz (kHz)-30 kHz and amplitude of 1 kV-4 kV.

9. The air decontamination device (100) as claimed in claim 6, wherein the DC power source and AC power source is of 1000 V-5000 V.

10. The air decontamination device (100) as claimed in claim 1, wherein when a distance between the positively charged conducting plate (108-1) and the negatively charged conducting plate (108-2) is 8 mm, the static electric field of 2.7 kV/cm is generated upon supplying a voltage of 2.16 kV to the plurality of conducting plates (108), or when a distance between the positively charged conducting plate (108-1) and the negatively charged conducting plate (108-2) is 8 mm, the static electric field of 4.2 kV/cm is generated upon supplying a voltage of 3.36 kV to the plurality of conducting plates (108).

11. The air decontamination device (100) as claimed in claim 1, wherein
when a distance between the positively charged conducting plate (108-1) and the negatively charged conducting plate (108-2) is 12 mm, the static electric field of 2.7 kV/cm is generated upon supplying a voltage of 3.24 kV to the plurality of conducting plates (108), or
when a distance between the positively charged conducting plate (108-1) and the negatively charged conducting plate (108-2) is 12 mm, the static electric field of 4.2 kV/cm is generated upon supplying a voltage of 5.04 kV to the plurality of conducting plates (108).

12. The air decontamination device (100) as claimed in claim 1, wherein the three dimensional material (110) is a fabric comprising a chemical agent coated thereon, wherein the chemical agent is selected from the group comprising: bactericides, fungicides, quaternary ammonium salts, such as 3-(trimethoxysilyl) propyl-N-octadecyl-N, N-5 dimethyl ammonium chloride, 3-(trimethoxysilyl) propyl-N-tetradecyl-N,N-dimethyl ammonium chloride, 3-(trimethoxysilyl) propyl-N,N-didecyl-N-methyl ammonium chloride, 3-(trihydroxysilyl) propyl-N-octadecyl-N,N-dimethyl ammonium chloride, or a combination thereof.

13. The air decontamination device (100) as claimed in claim 1, wherein the three dimensional material (110) is a composite material comprising multiple layers, wherein each layer of the multiple layers comprises surface moieties to cross-link with a chemical agent.

14. The air decontamination device (100) as claimed in claim 1, wherein a static electric field of 2.7 kV/cm is applied for 30 minutes to enhance the surface moieties dipole of the three dimensional material (110) to complete realignment to a direction of the static electric field in order to potentiate the microbial activity of the three dimensional material (110) to destroy the microbial cells that are trapped or deposited on the positively charged conducting plate (108-1) and the negatively charged conducting plate (108-2)

and to reduce a level of the microbial cells inside the decontamination unit (104) by over a billion fold.

15. A method of applying static electric field to an air decontamination device (100) to kill microbial cells and to reduce a level of microbial cell by over a billion fold, wherein the air decontamination device (100) comprises
an input unit (102) for receiving air from environment through a plurality of air inlet vents (114);
an output unit (103) for providing decontaminated air;
a decontamination cassette (104) that comprises
a first end (122) that is adapted to couple with the input unit (102), a second end (124) that is adapted to couple with the output unit (103);
a plurality of pairs of conducting plates (108), wherein each pair of conducting plates comprises a positively charged conducting plate (108-1), and a negatively charged conducting plate (108-2), wherein the positively charged conducting plate (108-1), and the negatively charged conducting plate (108-2) are charged when a static electric field that ranges from 2.7 KiloVolt/centimetre (kV/cm) to 4.2 kV/cm is applied, wherein the plane of the positively charged conducting plate (108-1) is aligned parallel to the plane of the negatively charged conducting plate (108-2), wherein the positively charged conducting plate (108-1) and the negatively charged conducting plate (108-2) are separated by a distance that ranges between 8 mm to 12 mm to form an airflow path (212) inside the decontamination unit (104); and
a three dimensional (3D) material (110) that is coupled to both surfaces of each of the positively charged conducting plate (108-1) and the negatively charged conducting plate (108-2), wherein the three dimensional material (110) comprises surface moieties for imparting microbiocidal activity to both surfaces of the positively charged conducting plate (108-1) and the negatively charged plate (108-2), said method comprising:

applying the static electric field in the range of 2.7 KiloVolt/centimetre (KV/cm) to 4.2 KV/cm for 15 minutes to 30 minutes, to functionally exert a force on the charged microbial cells present in the air and trap the oppositely charged microbial cells, on the positively charged conducting plate (108-1) and the negatively charged conducting plate (108-2), due to attraction between charges of the microbial cells and the charges of positively charged conducting plate (108-1) and the negatively charged conducting plate (108-2), and enhance the surface moieties dipole of the three dimensional microbiocidal material (110) to complete realignment to a direction of the static electric field to potentiate the microbial activity of the three dimensional material (110) to kill the microbial cells that are trapped or deposited on the positively charged conducting plate (108-1) and the negatively charged conducting plate (108-2) and to reduce a level of the microbial cells inside the decontamination unit (104) by over a billion fold.

* * * * *